United States Patent
Jönbrink (10) Patent No.: US 6,409,711 B1
(45) Date of Patent: Jun. 25, 2002

(54) BARRIER FOR AN ABSORBENT PRODUCT

(75) Inventor: Anna-Karin Jönbrink, Lerum (SE)

(73) Assignee: SCA Hygiene Products AB, Gothenberg (SE)

( * ) Notice: Subject to any disclaimer, the term of this patent is extended or adjusted under 35 U.S.C. 154(b) by 0 days.

(21) Appl. No.: 09/423,976

(22) PCT Filed: May 11, 1998

(86) PCT No.: PCT/SE98/00859

§ 371 (c)(1),
(2), (4) Date: Feb. 22, 2000

(87) PCT Pub. No.: WO98/53779

PCT Pub. Date: Dec. 3, 1998

(30) Foreign Application Priority Data

May 26, 1997 (SE) ................................................ 9701983

(51) Int. Cl.[7] ................................................ A61F 13/15
(52) U.S. Cl. ........................ 604/385.01; 604/385.101; 604/378
(58) Field of Search ........................... 604/378, 385.01, 604/385.101

(56) References Cited

U.S. PATENT DOCUMENTS

| | | | | |
|---|---|---|---|---|
| 5,792,130 A | * | 8/1998 | Widlund | 604/385.01 |
| 6,017,336 A | * | 1/2000 | Sauer | 604/385.01 |
| 6,123,692 A | * | 9/2000 | Guidotti | 604/385.01 |
| 6,152,907 A | * | 11/2000 | Widlund | 604/385.08 |

FOREIGN PATENT DOCUMENTS

| | | | |
|---|---|---|---|
| EP | 581044 | * | 2/1994 |
| EP | 670153 | | 9/1995 |
| WO | 9525493 | | 9/1995 |

* cited by examiner

*Primary Examiner*—John J. Calvert
*Assistant Examiner*—Angela J. Grayson
(74) *Attorney, Agent, or Firm*—Burns, Doane, Swecker & Mathis, L.L.P.

(57) ABSTRACT

The present invention relates to an absorbent product such as a diaper (1), pant diaper, incontinence shield or the like which has leg openings (8) and openings (17, 19) intended to receive urine and faces and which has a barrier in the form of a flap (39) between the openings (17, 19) to prevent faces coming into contact with urine. The barrier is made of material from one or more of the openings (8, 17, 19).

18 Claims, 5 Drawing Sheets

BARRIER FOR AN ABSORBENT PRODUCT

The present invention relates to an absorbent product such as a diaper, a pant diaper, an incontinence shield or the like, of the type according to the preamble of claim 1, and methods for making such products according to the preamble of claims 10 and 11.

An absorbent product of this type is known from WO-A 95/25493. A diaper made according to the teachings of this document comprises a top sheet of flexible material and a bottom sheet of liquid-impermeable material and an absorbent body contained between them. The top sheet is provided with a front and a rear longitudinal openings, the front opening being intended to receive urine and the rear opening being intended to receive faeces. The openings are separated by a bridge of top sheet material. The top sheet is free of connection to the absorbent body in the region of the openings. It is desirable in such products to prevent faeces coming into contact with the genitals of users particularly females users. In order to prevent faeces moving forward and coming into contact with the part of the absorbent body intended to receive urine an additional piece of flexible material is provided which extends transversely across the diaper between the absorbent body and the top sheet in the region between the two openings and which is fastened to both the absorbent body and the top sheet. This additional piece of material forms a barrier which prevents faeces from entering into the part of the absorbent body onto which urine is discharged and thus prevents faeces from coming into contact with the genitals of the user. The use of an additional piece of material to form such a barrier complicates the manufacturing process and leads to increased material costs.

An object of the present invention is to provide, in a simple and more cost-effective manner, a barrier which will help prevent faeces discharged onto the absorbent body moving forward into the region intended to receive urine.

This object is achieved by using the material which is cut out of the top sheet when forming the openings as the barrier material.

According to an embodiment of the invention the material which is cut to form one of the openings in the top surface is left attached to the top sheet at the end of the opening which is nearest to the other opening in order to form a flap or tongue of top sheet material. This flap is then bent, along its line of attachment with the top sheet, towards the absorbent body and the end and/or sides of the flap furthest away from the line of attachment are fastened to the absorbent body. In this way a barrier is formed without requiring any additional material.

In another embodiment of the invention the material in the form of a flap from one opening is used to form a first barrier as described above while the material in the form of a flap from the other opening is used to form a second barrier. This second flap is longitudinally slit to form two flap halves. These flap halves are first bent, along the line of attachment with the top sheet, towards the absorbent body and then folded at an angle to the line of attachment so that they project sideways. The ends and/or sides of the flap halves are then joined to the absorbent body at a lateral position which is preferably further from the longitudinal centreline of the product than the first barrier. In this way a barrier with a greater lateral reach is provided.

In a particularly advantageous embodiment of the invention one flap is displaced and attached to the underlying surface or absorbent body offset to one side of a longitudinal centre line while the other is displaced and attached offset to the other side of the longitudinal centre-line. In this way a zigzag path is provided between front and rear parts of the diaper. This effectively prevents faeces from moving forwards while at the same time it allows urine to pass back into the rear part of the diaper which increases the amount of absorption material available to receive urine.

In another embodiment of the invention the material which is cut to form one of the openings in the top surface is completely removed from the top surface to form a strip of material which is then fastened between the underside of the top surface and the absorbent body in a suitable position to form a barrier.

The invention will be described in more detail below with reference to the accompanying drawings of examples of embodiments, in which:

FIG. 3a shows a cross-sectional view along line III—III in FIG. 2a;

Figure 1:
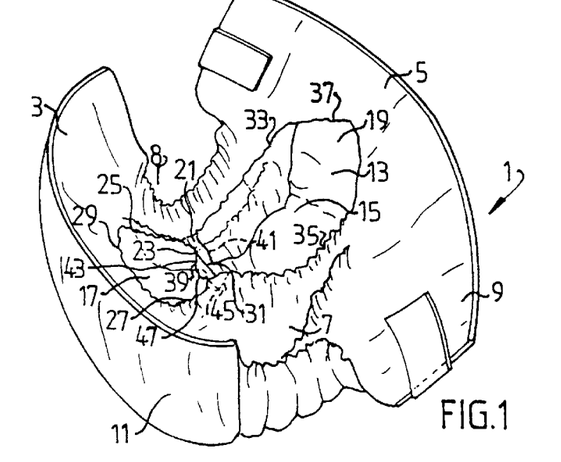
FIG. 1 shows a schematic perspective view, taken obliquely from above, of one embodiment of a diaper according to the invention.

FIG. 1 shows an embodiment of a diaper 1 having a barrier according to the invention. The diaper has a front portion 3, a rear portion 5, an intermediate crotch portion 7 and leg openings 8. The diaper comprises a top sheet 9, made of a, preferably liquid-impermeable, top sheet material such as spunbond or carded non-woven polypropylene fibres or so-called SMS-material (spunbond-meltblown-spunbond material), a bottom sheet 11, made of a, preferably liquid-impermeable, bottom sheet material, for example polythene film, and an absorbent body 13 comprised of a centre body 14 and absorbent side bodies 14' enclosed between the top sheet 9 and bottom sheet 1. Absorbent body 13 is in contact with bottom sheet 11 over substantially all of the surface of the absorbent body 13 facing towards the bottom sheet 11. A space 15 for the retention of emitted faeces and body fluids is provided between absorbent body 13 and the top sheet 9 over part of the surface of the absorbent body 13 which faces towards the top sheet 9. The top sheet 9 is provided with two openings 17, 19 separated by a bridge 21 of top sheet material. Bridge 21 is positioned in the crotch portion 7 of diaper I in a position intended to correspond to the region between the genitals and anus of an intended user. Urine opening 17 is provided in the front portion 3 of top sheet 9 in a position suitable for receiving urine emitted by a user. Urine opening 17 has a bridge end 23, two longitudinal sides 25, 27 and a distal end 29. Urine opening 17 is formed by removing out of top sheet 9 a piece of material (not shown) having the shape of. urine opening 17. Faeces opening 19 is provided in the rear portion 5 of top sheet 9 in a position suitable for receiving faeces excreted by the user. Faeces opening 19 has a bridge end 31, two longitudinal sides 33, 35 and a distal end 37. Faeces opening 19 is formed by cutting top sheet material 9 along the longitudinal sides 33, 35 and distal end 37 to form a flap or tongue 39 attached to bridge 21. Flap 39 has a bridge end 41, two longitudinal sides 43, 45 and a distal end 47. Flap 39 is bent downwards along bridge end 41 and distal end 47 of flap 39 is attached to absorbent body 13 in the crotch portion 7 of diaper 1. In this example the sides of the flaps and openings are shown as being substantially straight but they may be any suitable shape, for example, curved.

Figure 2A:
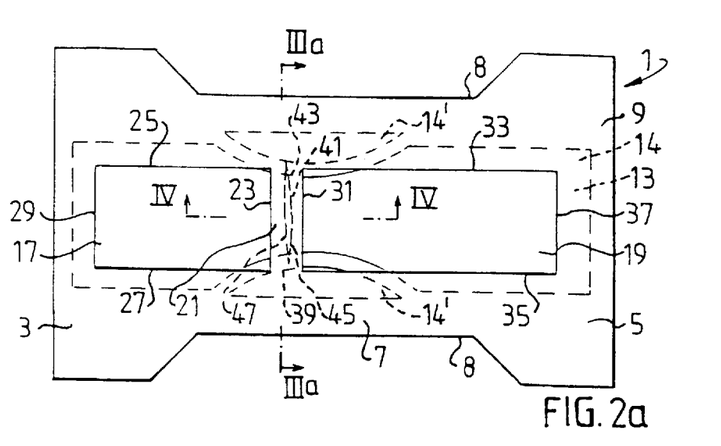
FIG. 2a shows a schematic illustration from above, of the diaper shown in FIG. 1 in a flat state.

FIG. 2a shows schematically in a view from above the diaper of FIG. 1 in a flat state. In this figure constructional features of the diaper which are not related to the present invention have been omitted for the sake of clarity.

Figure 2B:
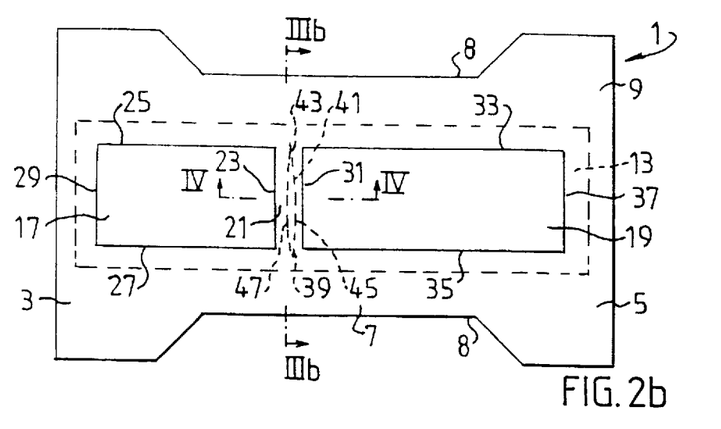
FIG. 2b shows a schematic illustration from above similar to that of FIG. 2a for a diaper without absorbent side bodies.

FIG. 2b shows an embodiment of a diaper similar to that shown in FIG. 2a which has a simpler absorbent body 14 which lacks absorbent side bodies 14'.

Figure 3A:
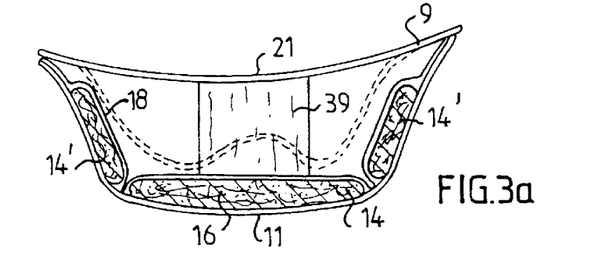

FIG. 3a shows a cross-sectional view along line IIIa—IIIa in FIG. 2a. It can be seen here that flap 39 extends from top surface 9 to absorbent body 13. For the sake of clarity of illustration absorbent bodies 13, 14 and 14' are shown simplified in this embodiment and are drawn as if they were made of a homogenous absorbent material 16 and a surface material 18 which covers the surface of the absorbent material which is intended to face top sheet 9. In this embodiment surface material 18 is shown attached to bottom-surface 11 between centre body 14 and side bodies 14, as well as between top surface 9 and bottom surface 11. This is not intended as a limitation to how absorbent bodies can be formed as it is naturally possible for them to consist of any sort of absorbent means comprised of one or more different materials and/or layers of material as will be described later. The expression absorbent body is therefore intended to refer to all parts of the diaper which are intended to absorb and/or retain fluid as well as to layers of material intended to:

attach these parts to the diaper; and/or, prevent them from being damaged; and/or prevent them coming into contact with the body of the user through holes made in said top sheet 9.

In this embodiment this distal end 47 of flap 39 is attached to absorbent body 13 symmetrically with respect to the longitudinal centre-line of the diaper 1. It does not extend laterally to the longitudinal edges of the absorbent body 13 and acts only as a barrier to the movement of faeces in the centre region of the absorbent body 13.

Figure 3B:
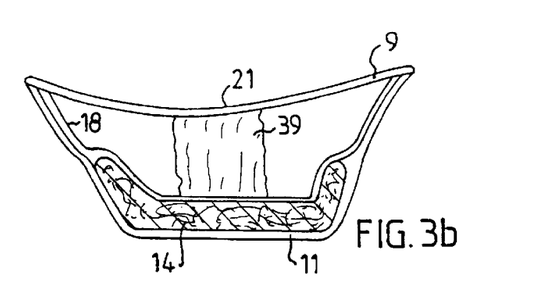
FIG. 3b shows a cross-sectional view similar to that of FIG. 3a for a diaper without absorbent side bodies.

FIG. 3b shows a cross-sectional view along line IIIb—IIIb in FIG. 2b.

Figure 4:
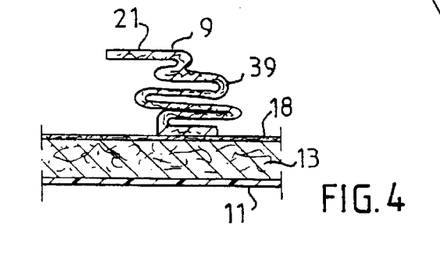
FIG. 4 shows a cross-sectional view along line IV—IV in FIG. 2.

FIG. 4 shows a cross-sectional view along line IV—IV in FIG. 2. It can be seen here that flap 39 is folded concertina fashion between bridge 21 and absorbent body 13. In order to ensure that flap 39 folds in a concertina fashion it can be advantageous to make the top sheet 9 from an elastic material or to provide the top sheet material with elastic means (not shown) at least in the longitudinal direction of the diaper and to pretension the material, at least in the longitudinal direction of the diaper, such that the flap 39 tends to draw up on itself after it has been cut out of the top sheet 9. Although flap 39 is shown attached to absorbent body 13 at a position under bridge 21 it is possible that it could be attached to the absorbent body 13 in any suitable position, for example, forward under the urine opening 17 and back under the faeces opening 19. Flap 39 does not have to be folded and can be made out of only part of the material cut out of faeces opening 19.

Although in this embodiment the barrier has been formed of a flap 39 made of the material from faeces opening 19 it is of course possible to use the material remaining from the making of urine opening 17 to form the barrier. It is also possible to use the material from both openings (or more openings which can be provided if necessary) to form a plurality of barriers and/or an extra thick barrier.

Figure 5:
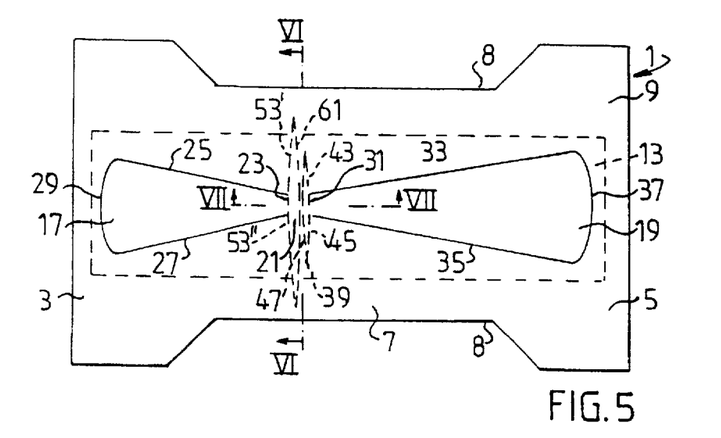
FIG. 5 shows a schematic illustration from above, of a second embodiment of a diaper according to the invention in a flat state.
Figure 6:
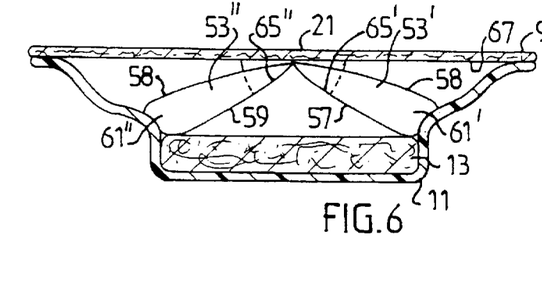
FIG. 6 shows a cross-sectional view along line VI—VI in FIG. 5.
Figure 7:
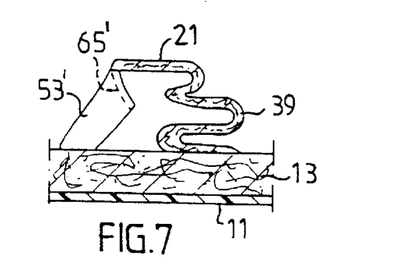
FIG. 7 shows a cross-sectional view along line VII—VII in FIG. 5.

A second embodiment of the invention is shown in FIGS. 5–7. Features of this embodiment which correspond to features in the embodiment shown in FIGS. 1–4 have the same reference numbers as used in FIGS. 1–4. Absorbent body 13 is shown here, for the sake of example only, as a simple absorbent body made of, for example, absorbent foam. In this embodiment the material from urine opening 17 is used to form a second flap 53. This flap 53 has a bridge end 55, two curved longitudinal sides 57, 59 and a distal end 61. This flap is cut along its longitudinal centre-line to form two substantially mirror-image partial flaps 53' and 53". Partial flap 53' has a bridge end 55', curved longitudinal side 57, straight longitudinal side 58 and distal end 61'. Partial flap 53" has a bridge end 55", straight longitudinal side 58, curved longitudinal side 59 and distal end 61". These partial flaps 53', 53" are intended to form barriers with a lateral reach greater than that of flap 39. This is achieved by bending partial flaps 53', 53" downwards towards absorbent body 13 and twisting each of them about an axis 65', 65" which is inclined to the longitudinal direction of the partial flaps 53', 53" so that the distal ends 61', 61" are displaced away from the longitudinal centre-line of the absorbent body 13. The distal ends 61', 61" can be attached to the longitudinal edges of absorbent body 13 and/or to bottom sheet 11.

In a variation of this embodiment, not shown, flap 39 is completely removed from bridge 21 and then attached by its longitudinal sides 43, 45 to the underside of bridge 21 and absorbent body 13. In this way a wider barrier can be achieved.

Figure 8:
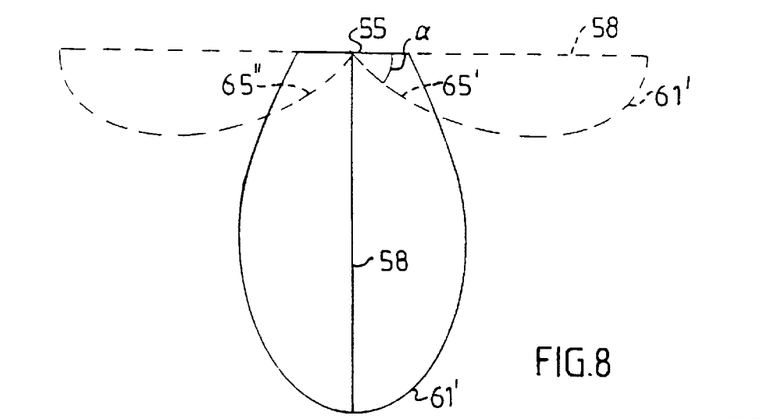
FIG. 8 shows a folding pattern for a further embodiment of a flap.

FIG. 8 shows a folding pattern for further embodiment of a flap 53 in which the axes 65', 65" are inclined at angle I=45/ to the longitudinal axis of the partial flaps 53', 53" such that the twisted partial flaps 53', 53" (shown by dotted lines) are essentially perpendicular to the plane of the bottom surface 67 of top sheet 9. If desired partial flaps 53', 53" can then be attached to the bottom surface 67 of top sheet 9.

Figures 9, 10:
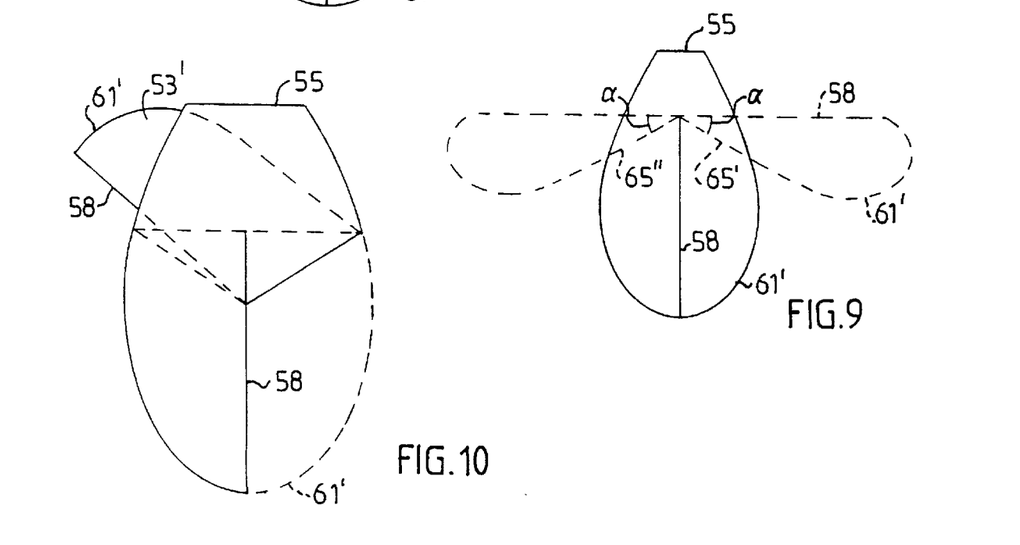
FIG. 9 shows a folding pattern for another embodiment of a flap.
FIG. 10 shows a partial folding pattern for yet another embodiment of a flap.

FIG. 9 shows a folding pattern of further embodiment of the invention in which the longitudinal cut which forms partial flaps 53', 53" does not extend all the way from distal end 61 to bridge end 55. In this way a barrier can be made which first extends vertically downwards before then extending laterally. This barrier can be attached to the absorption body by the fold lines 65' and/or by some or all of the edges of the partial flaps in order to provide a wider barrier.

FIG. 10 shows a intermediate position in a folding pattern of further embodiment of the invention in which only one of the partial flaps is shown folded. Here the longitudinal cut which forms partial flaps 53', 53" does not extend all the way from distal end 61 to bridge end 55 and the partial flaps 53', 53" are twisted laterally so that the distal end 61' of the right-hand flap 53' extends to the left and the distal end of the left-hand flap 53' extends to the right.

Figure 11:
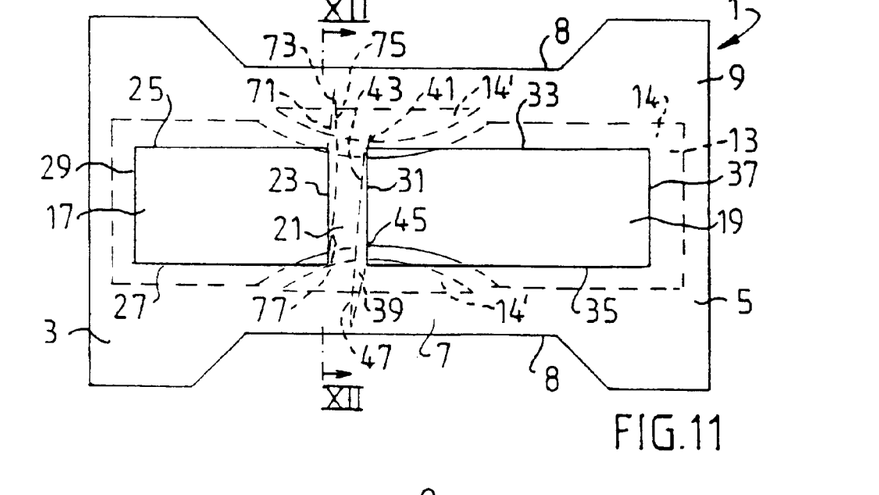
FIG. 11 shows a schematic illustration from above of a preferred embodiment of a diaper according to the invention.

FIG. 11 shows in plan view the preferred embodiment of a diaper according to the invention. This diaper is similar to the diaper shown in FIGS. 2–4 and the same reference numbers are used to refer to features which are common to both embodiments. In this embodiment the material from urine opening 17 is used to form a flap 71 hinged at bridge 21. Flap 71 has sides 73, 77 and a distal end 75. Flap 71 is folded and attached by its distal end 75 to the absorbent body 13 at one side of the longitudinal centre-line of the diaper 1 while flap 39 is attached to absorbent body 13 at the other side of the longitudinal centre-line of the diaper. In this way a non-symmetrical barrier is formed. In order to pass from one side of the barrier to the other side waste products must travel a zigzag path.

Figure 12A:
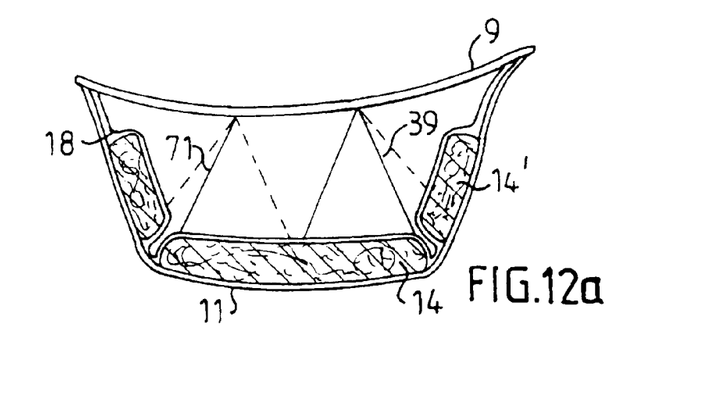
FIG. 12a shows a cross-section along line XII—XII in FIG. 11.

FIG. 12a shows a section along line XII—XII in FIG. 11. Dashed lines show how the flaps 39, 71 can be also attached to the side absorbent bodies 14' if there is sufficient flap material.

Figure 12B:
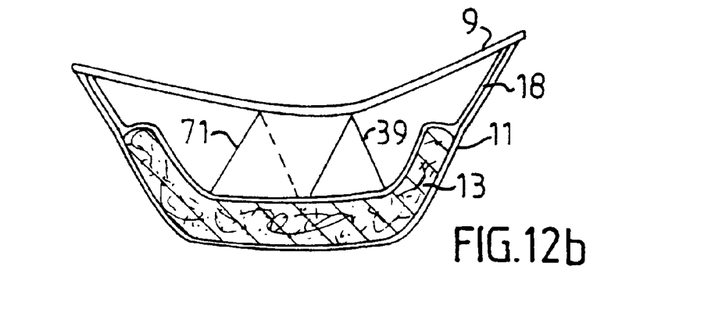
FIG. 12b shows a cross-section similar to that in FIG. 12a for a diaper without absorbent side bodies.

FIG. 12b shows a section corresponding to 12a for a diaper without side absorbent bodies 14'.

Figure 13A:
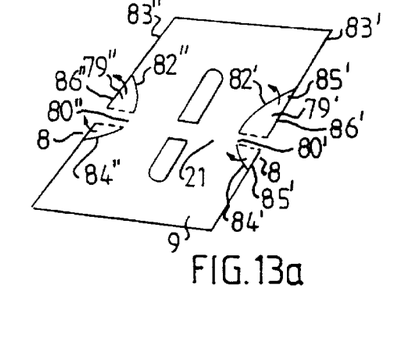
FIGS. 13a–d show schematically in perspective the steps for making a flap from the material present in leg openings.
Figure 13B:
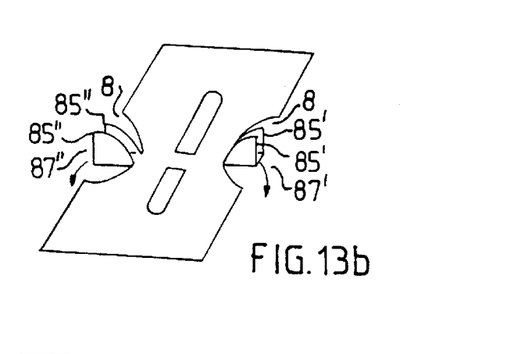
Figure 13C:
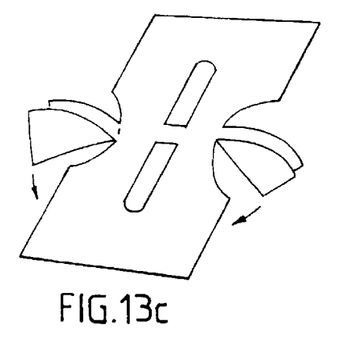
Figure 13D:
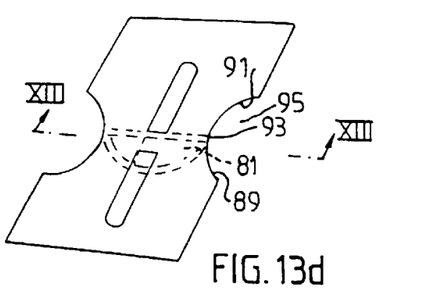
Figure 13E:
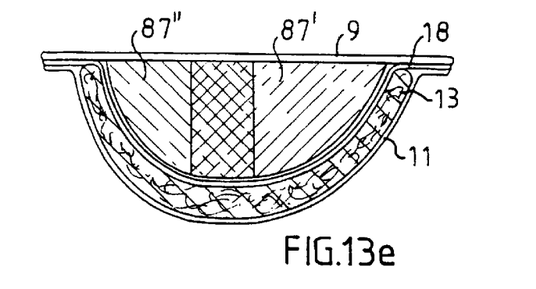
FIG. 13e shows a cross-section, similar to that shown in FIG. 3a, of the flap from FIG. 13d in a diaper.

FIGS. 13a–13d shows one embodiment of how the material 79', 79" from leg openings 8 in a piece of, for example, top sheet 9 material can be cut and folded to form a barrier 81. As is shown in FIG. 13a, each leg opening 8 is formed by cutting a curved flap 79', 79" of material from opposing longitudinal sides 83', 83" of the top sheet 9. The flaps 79', 79" are attached to, or remain attached to, the top sheet 9 by a bridge end 80', 80" in the bridge region 21. Each flap 79', 79" has longitudinal sides 82', 82", 84', 84" and a distal end 86', 86". In FIG. 13b it can be seen how the two tips 85' resp. 85" of each flap 79', 79" can be folded towards each other out of the plane of the top sheet 9 to form a half barrier 87', 87" having a double thickness of top sheet material. These half barriers 87', 87" can then be folded along their lines of attachment with the bridge 21 as shown in FIG. 13c until they meet, and possibly partly overlap, under the bridge 21, to form a barrier as shown in FIG. 13d. This barrier can be attached to the underside of bridge 21 and to the absorbent body when the diaper is assembled. Also shown in FIG. 13d are the sides 89, 91, bridge end 93 and distal ends 95 of leg openings 8. FIG. 13e shows a cross-section through a diaper after the absorbent body 13 and bottom layer 11 have been positioned under top sheet 9 but before they have been attached to the top sheet 9 and half barriers 87', 87".

It is of course possible to fold the flaps in other ways. It is also possible to only use material from one of the leg openings to form the barrier or to use a combination of barriers made from leg opening, urine opening and faeces opening material. It is also possible that the absorbent product is provided with only one opening for the reception of body fluids and faeces, in which case the barrier formed by the flap material from the leg openings can be used to divide the single opening into two so as to form separate body fluid and faeces receiving openings.

In order to achieve the best sealing between the body of the user between the genitals and anus and the top sheet of an absorbent product according to the invention it is important that the barrier does not tend to pull the top sheet away from contact with the body of the user. It is therefore preferable that the barrier be of sufficient depth such that even if the absorbent body is full of waste, and therefore tends to sag downwards, no downward forces are transmitted to the top sheet via the barrier. Advantageously the top sheet can be elastic, at least in the lateral direction, so as to tend to cling to the body of the user. The top sheet can be made of an elastic film which is pre-stretched before being attached to the rest of the absorbent product in order to give the required elastic force. Alternatively the top sheet can be made of one or more non-elastic films or sheets of material which are provided with suitably tensioned elastic means such as elastic threads or ribbons or the like. These elastic means can, for example, be provided only in the lateral or longitudinal directions of the finished product, or in both directions or in any direction. It is also possible for the top sheet to have different elastic means in different parts of the top sheet, for example, the top sheet could be laterally elastic in the front and rear parts and longitudinally elastic in the crotch part. It is however particularly advantageous for the elastic force to be provided in the direction which ensures that when a flap is attached between a top sheet and an absorbent body in an absorbent product then the elastic force is normal to the plane of the laid-out product. In other words the elastic force should tend to cause the flap to fold up on it self in a concertina-like way. Naturally this elastic force should be adapted such that it does not pull the top sheet away from the body of the user. It can therefore be appropriate that the elastic force in the lateral direction of the top sheet, at least in the crotch region, in an absorbent product be greater that the elastic force in the longitudinal direction so as to overcome the downwards force exerted by the flap.

Figure 14:
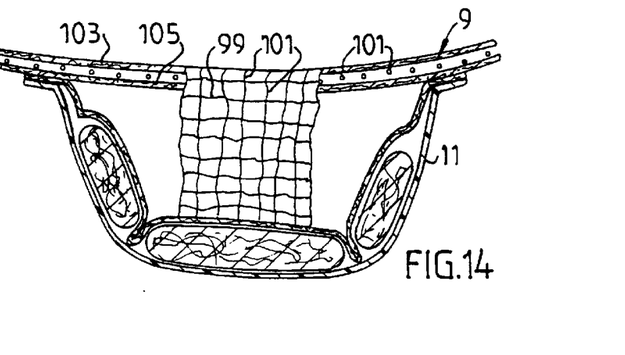
FIG. 14 shows a cross-section similar to those shown in FIGS. 3a and 3b of an other embodiment of a diaper according to the invention.

An example of a diaper according to the invention provided with an elastic top sheet is shown in FIG. 14. The top sheet 9 comprises an elastic net of lateral elastic fibres 99 and longitudinal elastic fibres 101 between a top surface layer 103 and a bottom surface layer 105. The fibres 99, 101 are preferably pre-stressed, for example, by being stretched before being attached to one or more of the surface layers 103, 105. It the longitudinal fibres 101 are attached along the whole of their length while the lateral fibres 99 are only attached by their ends then it is possible to cut out flaps which are elastically tensioned substantially only in the longitudinal direction.

Top surface layer 103 and bottom surface layer 105 can be of any suitable material, such as a liquid-impermeable non-woven and preferably are joined to each other (not shown for reasons of clarity in the FIG. 14) in the regions between the elastic fibres 99, 101. This joining can be accomplished by, for example, gluing, heat-sealing, ultrasonic bonding or any other suitable means. In this embodiment the top sheet 9 extends out beyond the boundary of the bottom sheet 11.

In the case of a diaper according to the invention in which the top sheet has regions of different elasticity, e.g. regions where there is a greater elastic pre-stress in one direction than in another direction it is possible to use only part of the top sheet material removed from an opening to form the flap. Thus if the top sheet material in the crotch region is longitudinally pre-stressed while the front and rear regions are laterally pre-stressed then the part of the flap which is formed of material from the front or rear regions will tend to fold laterally while the part from the crotch region will tend to fold up longitudinally. In order to avoid problems which may occur when attempting to fasten a laterally folded end of a flap to another surface, e.g. the bottom surface, it can be advantageous to remove the laterally pre-stressed material from the flap and only use the longitudinally pre-stressed portion to form the barrier.

While the invention has been illustrated by examples of diapers it is also applicable to other types of absorbent products such as a pant diaper, an incontinence shield or the like. The embodiments shown above can be modified within the scope of the invention for example, by changing the shapes of the openings, the number of openings and their sizes. Furthermore the flaps can be cut to form more than two partial flaps and the partial flaps do not have to be symmetrical nor do they have to be placed symmetrically. Partial flaps can also be optionally provided at both or all openings. It is also possible to vary their attachment to other parts of the absorbent product so that they can be attached by their sides and/or ends to any of the constituent parts of the product. Flaps can have straight or curved sides and/or edges. Flaps can also be attached directly to the bottom layer if necessary or desired, for example if the absorbent body consists of two elongated absorbent means positioned on either side of the longitudinal centre-line of the diaper and separated by an exposed top surface of the bottom layer then, in order to block the central region of the diaper, it is necessary that a flap is attached to this exposed top surface of the bottom layer. A similar situation occurs if the absorbent body consists of two or more absorbent means positioned on either side of a lateral dividing line, for example in the case where separate absorbent means are provided at the front and rear of the diaper for liquid, respectively, solid waste.

The invention is not limited to using material from the opening in the top sheet but it is also conceivable to form the barrier flaps from other material which would normally be wasted during manufacture. An example of such material is the material removed to form leg openings in the bottom sheet.

The invention is suitable for use with absorbent bodies of any type, for example, absorbent bodies made of one or more absorbent materials for example, cellulose fluff with or without super absorbent polymer, absorbent foam and can comprise one or more layers of absorbent material and, if necessary, further layers of absorption enhancing, wicking or chaffing preventing material.

It is naturally possible for the skilled man to combine features from the various embodiments, which are shown an described merely as non-limiting examples, as required. Thus it is, for example, possible to use a top sheet made of an elastic laminate of non-woven, elastic fibre and non-woven layers with any type of barrier construction and any type of absorbent body.

The barrier can be attached by any suitable means such, but not limited to, adhesive bonding, heat sealing, welding, ultrasonic bonding, sewing and such means can also be used to join together the other constituent parts of the absorbent product.

The materials used for the absorbent product are preferably recyclable, biologically degradable and/or made from renewable resources.

What is claimed is:

1. Absorbent product (1) such as a diaper, a pant diaper, an incontinence shield or the like comprising a front portion (3), a rear portion (5) and an intermediate crotch portion (7) wherein said absorbent product (1) includes a top sheet (9), made of a top sheet material, which is intended to face towards the user when the product is worn, a bottom sheet (11) which is intended to face away from the user when the product is worm, and an absorbent body (13) between said top sheet (9) and said bottom sheet (11), wherein said top sheet (9) is provided with at least two openings comprising urine opening (17), faeces openings (19) and optionally leg openings (8), separated by a bridge (21) of top sheet material, each said opening (8, 17, 19) having a bridge end (23, 1, 93), a distal end (29, 37, 95) and two sides (25, 27, 33, 35, 89, 91) characterised in that a flap (39; 53, 71, 79', 79", 81) of top sheet material, having a bridge end (41; 55, 80', 80"), longitudinal sides (43, 45; 57, 58, 59, 82', 82", 84', 84") and a distal end (47; 61, 86', 86"), and which is cut out to form at least one of said openings (8, 17, 19), is attached by one of said ends (41, 47, 55, 61, 80', 80", 86', 86") or said sides (43, 45; 57, 58, 59, 82', 82", 84', 84") to said bridge (21) and wherein said flap (39; 53, 71, 79', 79", 81) is fastened to said absorbent body (13) and/or said top sheet (9) and/or said bottom sheet (11) by another of said ends (41, 47, 55, 61 80', 80", 86', 86") and/or said longitudinal sides (43, 45; 57, 58, 59, 82', 82", 84', 84").

2. Absorbent product (1) according to claim 1 characterised in that said flap (39; 53, 71, 79', 79", 81) is integrally attached at said bridge end (41; 55, 80', 80") to said bridge (21) and is fastened to said absorbent body (13) and/or said top sheet (9) and/or said bottom sheet (11) by said distal end (47; 61, 86', 86") and/or said longitudinal sides (43, 45; 57, 58, 59, 82', 82", 84', 84").

3. Absorbent product (1) according to claim 1 characterised in that said flap (53,) of top sheet material, having a bridge end (55), longitudinal sides (57, 59) and a distal end (61), and which is cut out to form at least one of said openings (17, 19), is attached at-said bridge end (55) to said bridge (21) and wherein said flap (53) is longitudinally divided to form two partial flaps (53', 53"), each having a distal end (61', 61") and longitudinal sides (57, 58, 59) and wherein at least one of said partial flaps (53', 53") is fastened to said absorbent body (13) or said top sheet (9) or said bottom sheet (11) by said distal end (61', 61") and/or said longitudinal sides (57, 58, 59).

4. Absorbent product (1) according to claim 1 characterised in that there are two flaps(39; 53, 71, 79', 79", 81).

5. Absorbent product according to claim 4 characterised in that said flaps (39; 53, 71, 79', 79", 81) are fastened to said absorbent body (13) or said top sheet (9) or said bottom sheet (11) by said distal end (61', 61") and/or said longitudinal sides (57, 58, 59) offset to opposite sides of the longitudinal centre-line of said product.

6. Absorbent product according to claim 1 characterised in that at least one of said openings is a leg opening (8).

7. Absorbent product according to claim 1 characterised in that said openings are openings (17, 19) for the reception of body wastes.

8. Absorbent product according to claim 1 characterised in that at least one of said flaps (39, 71, 79', 79", 81) or partial flaps (53', 53") is attached laterally spaced from the longitudinal centre-line of the product.

9. Absorbent product according to claim 1 characterised in that said flap (39, 71, 79', 79", 81) or said partial flaps (53', 53") is/are elastic in the direction normal to the plane of the bottom sheet (11).

10. Absorbent product (1) such as a diaper, a pant diaper, an incontinence shield or the like comprising a front portion (3), a rear portion (5) and an intermediate crotch portion (7) wherein said absorbent product (1) includes a top sheet (9), made of a top sheet material, which is intended to face towards the user when the product is worn, a bottom sheet (11) which is intended to face away from the user when the product is worn, and an absorbent body (13) between said top sheet (9) and said bottom sheet (11), wherein said top sheet (9) is provided with at least two openings comprising urine opening (17), faeces openings (19) and optionally leg openings (8), separated by a bridge (21) of top sheet material, each said opening (8, 17, 19) having a bridge end (23, 31, 93), a distal end (29, 37, 95) and two sides (25, 27, 33, 35, 89, 91) characterised in that a flap (39, 53, 71, 79', 79") of top sheet material which is cut out of said top sheet (9) to form at least one of said openings (8, 17, 19), is attached by an end (41, 47, 55, 61, 80', 80", 86', 86") or side (43, 45; 57, 58, 59, 82', 82", 84', 84") to said bridge (21) and wherein said flap (39, 53, 71, 79', 79") is fastened to said absorbent body (13) and/or said top sheet (9) and/or said bottom sheet (11) by another end (41, 47, 55, 61 80', 80", 86', 86") and/or longitudinal sides (43, 45; 57, 58, 59, 82', 82", 84', 84") to form a barrier (39; 53, 71, 79', 79", 81) between said urine opening (17) and said faeces opening (19).

11. Absorbent product according to claim 10 characterised in that said flap (39, 71) does not extend across the whole width of the absorbent body (13).

12. Method for forming a barrier (39; 53, 71, 79', 79", 81) in between a top sheet (9) and an absorbent body (13) in an absorbent product (1) such as a diaper, a pant diaper, an incontinence shield or the like comprising a front portion (3), a rear portion (5) and an intermediate crotch portion (7) wherein said absorbent product includes a top sheet (9) made of a top sheet material which is intended to face towards the user when the product is worn, a bottom sheet (11) which is intended to face away from the user when the product is worn and an absorbent body (13) between said top sheet (9) and said bottom sheet (11), wherein said top sheet (9) is provided with two openings (8, 17, 19), separated by a bridge (21) of top sheet material, each said opening (8, 17, 19) having a bridge end (23, 31, 93), a distal end (29, 37, 95) and two longitudinal sides (25, 27, 33, 35, 89, 91) characterised by the steps of:

forming one of said openings (8, 17, 19) by cutting out a flap (39; 53, 71, 79', 79", 81) in the top sheet (9), the flap (39; 53, 71, 79', 79", 81) having a bridge end (41, 55, 80', 80"), a distal end (47, 61, 86', 86") and two longitudinal sides (43, 45, 57, 58 ,59, 82', 82", 84', 84");
   attaching said bridge end (41, 55, 80', 80") of said flap (39; 53, 71, 79', 79", 81) to the top sheet (9) by said bridge (21);
   fastening said distal end (47, 61, 86', 86") of said flap (39; 53, 71, 79', 79", 81) to said absorbent body (13) and/or top sheet (9) and/or bottom sheet (11).

13. Method for forming a barrier (39; 53, 71, 79', 79", 81) between a top sheet (9) and an absorbent body (13) in an absorbent product (1) such as a diaper, a pant diaper, an incontinence shield or the like comprising a front portion (3), a rear portion (5) and an intermediate crotch portion (7) wherein said absorbent product includes a top sheet (9) made of a top sheet material which is intended to face towards the user when the product is worn, a bottom sheet (11) which is intended to face away from the user when the product is worn and an absorbent body (13) between said top sheet (9) and said bottom sheet (11), wherein said top sheet (9) is provided with two openings (8, 17, 19), separated by a bridge (21) of top sheet material, each said opening (8, 17, 19) having a bridge end (23, 31, 93), a distal end (29, 37, 95) and two longitudinal sides (25, 27, 33, 35, 89, 91) characterised by the steps of:

forming one of said openings (8, 17, 19) by cutting a flap (39; 53, 71, 79', 79", 81) in the top sheet (9), the flap (39; 53, 71, 79', 79", 81) having a bridge end (41, 55, 80', 80"), a distal end (47, 61, 86', 86") and two longitudinal sides (43, 45, 57, 58, 59, 82', 82", 84', 84") wherein said flap (39; 53, 71, 79', 79", 81) is integrally attached at said bridge end (41, 55, 80', 80") to said bridge (21);
   folding said flap (39; 53, 71, 79', 79", 81) along an axis formed by said bridge end (41, 55, 80', 80") in a direction towards said absorbent body (13);
   fastening said distal end (47, 61, 86', 86") and/or one of said longitudinal sides (43, 45, 57, 58, 59, 82', 82", 84', 84") of said flap (39; 53, 71, 79', 79", 81) to said absorbent body (13) and/or top sheet (9) and/or bottom sheet (11).

14. Method according to claim 12 characterised by the steps of:

cutting said flap (53) in the longitudinal direction along a line extending from said distal end (61) towards the bridge end (55) to form two partial flaps (53', 53");
   folding each of the partial flaps (53', 53") along a respective fold axis (65', 65") which is inclined at an angle to said line such that the distal end (61', 61") of each partial flap (53', 53") is transversely displaced to one side of the longitudinal centre-line of said flap (53);
   fastening said distal end (61', 61") of each partial flap (53', 53") to said absorbent body (13) and/or top sheet (9) and/or bottom sheet (11).

15. An absorbent product according to claim 1, wherein the absorbent product is one of a diaper, a pant diaper, and an incontinence shield.

16. An absorbent product according to claim 10, wherein the absorbent product is one of a diaper, a pant diaper, and an incontinence shield.

17. Method according to claim 12, wherein the absorbent product is one of a diaper, a pant diaper, and an incontinence shield.

18. Method according to claim 13, wherein the absorbent product is one of a diaper, a pant diaper, and an incontinence shield.

* * * * *